(12) United States Patent
Mesmin et al.

(10) Patent No.: US 7,169,370 B2
(45) Date of Patent: Jan. 30, 2007

(54) METHOD FOR CO-PRECIPITATING ACTINIDES AND METHOD FOR PREPARING MIXED ACTINIDE OXIDES

(75) Inventors: Claire Mesmin, Le Garric (FR); Alain Hanssens, Tresques (FR); Charles Madic, Thiais (FR); Pierre Blanc, Les Angles (FR); Marie-Francois Debreuille, Marcoussis (FR)

(73) Assignees: Commissariat a l'Energie Atomique, Paris (FR); Compagnie Generale des Matieres Nucleaires, Velizy-Villacoublay (FR)

( * ) Notice: Subject to any disclaimer, the term of this patent is extended or adjusted under 35 U.S.C. 154(b) by 457 days.

(21) Appl. No.: 10/381,592

(22) PCT Filed: Oct. 4, 2001

(86) PCT No.: PCT/FR01/03056

§ 371 (c)(1), (2), (4) Date: Apr. 2, 2003

(87) PCT Pub. No.: WO02/28778

PCT Pub. Date: Apr. 11, 2002

(65) Prior Publication Data

US 2004/0021132 A1 Feb. 5, 2004

(30) Foreign Application Priority Data

Oct. 5, 2000 (FR) .................................. 00 12727

(51) Int. Cl.
- *C01G 1/00* (2006.01)
- *C01G 43/00* (2006.01)
- *C01G 56/00* (2006.01)

(52) U.S. Cl. ............................ 423/3; 423/11; 423/12; 423/15; 423/251; 423/254; 252/643

(58) Field of Classification Search ............. 423/3, 423/11, 12, 15, 251, 254; 376/170, 172, 376/180, 181, 409; 252/643

See application file for complete search history.

(56) References Cited

U.S. PATENT DOCUMENTS

| | | | | |
|---|---|---|---|---|
| 3,168,601 A | * | 2/1965 | St Pierre | ...................... 264/0.5 |
| 3,287,279 A | * | 11/1966 | Lyon | .......................... 252/643 |
| 3,327,027 A | * | 6/1967 | St. Pierre | .................... 264/0.5 |
| 4,131,527 A | | 12/1978 | Friedman et al. | |
| 4,839,149 A | | 6/1989 | Madic et al. | |
| 4,923,639 A | * | 5/1990 | Stoll et al. | ..................... 588/18 |
| 5,841,200 A | * | 11/1998 | Bauer et al. | ................. 264/0.5 |

FOREIGN PATENT DOCUMENTS

| | | |
|---|---|---|
| EP | 0 251 399 | 1/1988 |
| GB | 978 615 | 12/1964 |
| WO | 97 25721 | 7/1997 |

OTHER PUBLICATIONS

K.M. Michael et al.; "Recovery of plutonium from oxalate supernatant by co-precipitation using uranous nitrate" BARC/E/016 1996.

R.D. Banushali: "Removal of plutonium and americium from oxalate supernatants by co-precipitation with thorium oxalate" Journal of Radioanalytical and Nuclear Chemistry, vol. 240, No. 3, pp. 977-979, 1999.

C. Keller et al.: "Ueber karbonatokomplexe des dreiwertigen americiums sowie desdes vier- und sechswertigen urans und plutonium" Radiochimica Acta, vol. 11, No. 3-4, pp. 123-127, 1969.

Y. Atlas et al.: "Preparation of homogeneous (Th0.8U0.2)O2 pellets via coprecipitation of (Th,U)(C2O4)2 nH2) powders" Journal of Nuclear Materials, vol. 249, pp. 46-51, 1997.

* cited by examiner

*Primary Examiner*—Timothy C. Vanoy
(74) *Attorney, Agent, or Firm*—Oblon, Spivak, McClelland, Maier & Neustadt, P.C.

(57) ABSTRACT

The present invention generally relates to the preparation of mixed actinide oxides, such as mixed oxides of uranium and plutonium (U, Pu) $O_2$, by simultaneously coprecipitation and then calcinations.

54 Claims, No Drawings

METHOD FOR CO-PRECIPITATING ACTINIDES AND METHOD FOR PREPARING MIXED ACTINIDE OXIDES

The present invention concerns a process for coprecipitating actinides in oxidation state (IV).

The invention concerns, in addition, a process for preparing mixed actinide oxides.

The technical field of the invention may, in a general manner, be defined as that of preparing mixed actinide oxides, in particular the mixed oxide of uranium and plutonium $(U, Pu)O_2$. The invention concerns, more precisely, the manufacture of said mixed oxides by coprecipitation, then calcination.

In fact, it is known that plutonium, usually mixed with uranium, constitutes an energetic material that may be recycled, either in "light water" type reactors, or in new generation reactors (such as rapid neutron reactions, or others). Said strategy presents a certain number of advantages. In particular, it allows savings in fissile material and constitutes a means of slowing down the undesired growth of the stock of plutonium. The recycling of plutonium in pressurised water reactors (PWR) has thus become an industrial reality that is reflected from one year to the other by the fact that an increasing proportion of the nuclear power reactors in existence is charged by means of assemblies using a mixed oxide of uranium and plutonium, called MOX $(UO_2-PuO_2)$ The extension of the use of MOX fuel necessitates both properly controlling the quality and the reliability of the production and the permanent improvement of the performances of said fuel in the reactor.

At present, the powders used in the manufacture of said MOX are prepared by mechanical mixing of $UO_2$ and $PuO_2$ oxides. The resulting mixture makes it possible, after pressing, sintering and precision grinding, to produce pellets of MOX fuel which meet current specifications.

The most tried and tested industrial process, known as the MIMAS process, comprises two principal stages in the preparation of the powders: a co-grinding of uranium and plutonium oxide powders to produce a first mixture, called the masterbatch, which is characterised by a plutonium level of 25 to 30%, then a dry dilution of said masterbatch in uranium oxide, up to the final desired level of plutonium.

For the manufacture of fuels, the powders used must meet precise characteristics. They must, in particular, have good flowability, good compressibility characteristics and be suitable for densification by fritting. An important quality criterion in the final properties of the fritted material is the homogeneity of the distribution of the plutonium.

A good homogeneity, in each fritted pellet, is, firstly, entirely favourable for the behaviour of the MOX in the reactor, particularly with a view to increasing the burnup fractions, and facilitates, secondly, the complete dissolution of the irradiated fuel during reprocessing operations.

The co-conversion, through the intermediary of the precipitation or the denitration of the uranium and the plutonium in solution, is one means that also allows an oxide $(U, Pu)\,O_2$ to be obtained after calcination.

The co-conversion process has, in comparison to the previous process of mechanical mixing, a certain number of potential advantages:

in principle, obtaining more easily, within each pellet, a very good homogeneity in the distribution of U and Pu elements;

reducing the number of stages, and simplifying the technology used in the production of the MOX fuel with the conceivable elimination of the grinding and mechanical homogenisation stages;

reducing the amount of process rejects and waste;

reducing the accessibility to the plutonium, and thus the risks of proliferation during the prior storage phase of the nuclear materials.

Among the processes for the co-conversion of actinides into oxides, one can schematically distinguish two major families: processes involving precipitation and processes involving thermal denitration.

The second type of process, which does not directly concern the field of the invention, makes it possible to obtain co-oxides by direct evaporation and calcination of nitric solutions. Said denitration processes, although simple in concept, generally result in products of relatively mediocre quality, which quite frequently necessitate the use of additives and/or additional mechanical or thermal treatments at a later stage.

Precipitation processes, or more precisely coprecipitation processes, involve the intermediate preparation of an insoluble salt, which is then separated and calcinated, in order to obtain the desired oxide. Said processes normally result in, after calcination, oxides of better quality, which allows the production of fritted pellets with a limited number of process stages. They make it possible to attain, unlike thermal denitration processes, an additional decontamination factor for uranium and plutonium. Said factor is more or less high depending on the precipitating reagent and the conditions of its use.

In order for a coprecipitation process to be practicable, while conserving a high interest, a certain number of requirements must be met:

conditions must exist that ensure a comparable and sufficiently high level of solubility of the elements mixed in solution before precipitation;

conditions must exist that ensure a comparable and sufficiently high level of solubility of the elements during precipitation;

the precipitation kinetics of said elements must be substantially identical;

the insoluble salts used must not be too stable or too unstable for the calcination stage to take place easily and in a safe manner;

the management of by-products must not present insurmountable difficulties.

In all coprecipitation processes, one normally distinguishes, in the case of actinides, in particular uranium and plutonium, two families: that in which the two elements are in separate oxidation states and that in which they are in the same oxidation state.

As regards processes in which the actinides, such as U and Pu, are in different redox states, the most commonly encountered form in reprocessing corresponds to the pair U (VI)-Pu (IV) which one obtains easily in nitric solution. The mixture U (IV)-Pu (III) is also accessible in solution, by ensuring that reducing conditions are maintained.

Coprecipitation processes, based on said pairs of U and Pu in solution, bring into play actinide ions that do not have the same structure. As a consequence, the precipitates obtained do not correspond to a perfect co-crystallisation of the uranium and the plutonium. As a result, the homogeneity of the distribution of the plutonium is intrinsically limited. One may cite, for example, the process of "U (VI)-Pu (IV) synprecipitation" in an ammoniacal medium, in which are formed a plutonium hydroxide and ammonium diuranate, which provide non-homogeneous oxide powders, requiring cumbersome mechanical treatments.

Moreover, the phenomena of non-simultaneous precipitation and the differences in solubility, observed under these conditions, constitute inherent defects in all of said processes. One may cite, as an example, the case of oxalic precipitation where one observes:

a significant difference in solubility between uranyl oxalate (U (VI)) and plutonium (IV) oxalate;

an interval between the respective fields of precipitation of the plutonium (III) oxalates and uranium (IV) oxalates.

Moreover, the solubility of said salts of uranium and plutonium is not influenced in an identical manner by the parameters of the process, such as the acidity or others.

As regards the processes, in which the actinides, such as U and Pu, are in the same redox states, it turns out that, in the insoluble salt that one wishes to obtain, the identical structure of the two metallic ions allows a true co-crystallisation of the uranium and the plutonium, which must make it possible to result in, after the stage of calcinating said salt, a preformed solid solution. Obtaining homogeneous mixed oxides is, therefore, under these conditions, largely facilitated.

The shared oxidation state of the actinides, such as U and Pu, may be the state VI, the usual precipitant is then ammonia combined, or not, with carbonate ions.

Said route has been more specifically developed in the process, called the AUPuC process, which makes it possible, from the double carbonate of ammonium, to obtain mixed oxides $(U, Pu)O_2$ of good quality.

Another possibility employs the precipitation of the mixed uranyl and plutonyl carbonate, which can also provide products of worthwhile quality. Although the analogue of the plutonium of ammonium diuranate is not known, it is also possible to obtain a real U, Pu ammoniacal coprecipitation by substitution of a part of U (VI) by Pu (VI).

The main disadvantages of said processes is the generation of supernatants that are one at the same time voluminous, awkward and often difficult to filter, as well as the difficulties of a valence adjustment in plutonium (VI).

Moreover, processes exist that bring into play the double oxalate of ammonium and uranium-plutonium, which constitutes a route to the mixed U-Pu oxide in the ratio 1/1. The difficulties linked to the lack of stability and the relatively high solubility of the actinide (VI) oxalates do not facilitate the development of this type of process.

The shared oxidation state of the actinides, such as U and Pu, may also be state IV.

A first difficulty, which generally turns out not to be too much of a hindrance, is then linked to the necessity of maintaining reducing conditions in order to conserve the reduced oxidation state (IV) of the uranium, despite the presence of oxidants, such as oxygen from the air, nitric acid and nitrous acid, most usually. The use of anti-nitrous compounds, such as hydrazine, constitutes the usual means allowing the stabilisation of the U (IV), without hindering the precipitation.

The principal difficulty resides in the necessary coexistence, within the aqueous solution, before precipitation, of the actinide ions in oxidation state IV. In fact, said ions, in the aqua form, inter react, according to the following reaction (1):

$$U\ IV + Pu\ IV \rightarrow U\ VI + Pu\ III \qquad (1)$$

This reaction is spontaneous in solution and constitutes a redhibitory obstacle to the coprecipitation of actinides in oxidation state IV.

It is possible to avoid said reaction by adding into the solution complexing agents that are very powerful, while at the same time sufficiently selective, towards actinides IV.

In this manner, by strongly displacing the normal potentials of the corresponding redox pairs, one succeeds in obtaining the crossover of said normal potentials.

In the case of U and Pu, phosphates or lacunar heteropolyanion type complexing agents such as phosphotungstate $P_2W_{17}O_{61}^{10-}$ meet said objective of joint stabilisation of U (IV) and Pu (IV) based on the thermodynamic concept of redox potentials. However, said complexing agents do not meet the concept, termed "CHON", and therefore lead to a pollution of the end products by the mineral elements present in said complexing agents.

Thus, they cannot be used in the nuclear field, in particular, for the manufacture of MOX type fuels.

It will be seen later that, in a specific embodiment of the invention, it is possible to obtain under appropriate conditions the same phenomenon of selective complexation leading to a crossover of redox potentials, but in a surprising manner, by using CHON complexing agents, thus eliminated later during the calcination stage.

Among the documents illustrating the coprecipitation of actinides, the following documents may be cited:

The document of KM. MICHAEL, PS. DHAMI "Recovery of plutonium from oxalate supernatant by coprecipitation using uranous nitrate" BARC/1996/E: 016 (1996) describes the recovery, by coprecipitation of plutonium, contained in the oxalic stock solutions arising from its conversion, by addition of uranous nitrate to said stock solutions.

The aim pursued in this document, is fundamentally to reduce the losses of plutonium in the precipitation stock solutions, by provoking a second precipitation of plutonium, and not of manufacturing, through a single coprecipitation, the compounds capable of providing by calcination a mixed oxide, such as $(U, Pu)O_2$, perfectly homogeneous.

In the same way, the document of R D. BANUSHALI, I C. PIUS, S K. MUJERKEE, V N. VAIDYA "Removal of plutonium and americium from oxalate supernatants by coprecipitation with thorium oxalate", Journal of radioanalytical and nuclear chemistry 240, (3), 977–979 (1999) concerns the combined recovery of plutonium and americium in oxalate supernatants by addition of thorium oxalate to said supernatants, then coprecipitation.

The aim pursued in this document is similar to that of the preceding document. It involves reducing the losses in plutonium and in amercium in oxalic stock solutions for precipitating Pu and Am, while at the same time ensuring the confinement of said two radioelements in a solid matrix.

The document of C. KELLER, D. FANG, "Uber Karbonatokomplex des dreiwertigen Americiums sowie des vier und sechs wertigen Urans und Plutoniums", Radiochimica Acta 11, 3–4, pp. 123–127 (1969), concerns a means of obtaining a homogenous precipitate $(U, PU)O_2$. The uranium and the plutonium, initially in state VI, are jointly reduced to oxidation state IV by an electrolysis in alkaline medium, in the presence of carbonate.

The resulting carbonated complexes are then precipitated and decomposed into oxide by heating under vacuum. The main disadvantages linked to said process are the necessity of working in alkaline medium and the complexity of the calcination operation.

The document EP-A-0 251 399 concerns the preferential precipitation of plutonium from an organic phase, par example TBP, diluted, charged with plutonium and uranium, by addition of an aqueous mixture of oxalic acid and nitric acid. The precipitated plutonium oxalate is dried and transformed by heating into plutonium oxide.

In said process, the uranium, which very partially accompanies the plutonium in the final compound formed, is found, in the organic phase, in oxidation state VI, whereas the plutonium is in oxidation state IV. Said final compound does not have the optimum qualities desired for obtaining perfectly homogeneous mixed oxides.

The document WO-A-97/25721 concerns the joint precipitation of uranium and plutonium, in order to separate them from the rest of the elements present in a solution of irradiated fuels. The process brings into play carboxylic acids or polycarboxylic acids, in order to precipitate the uranium in oxidation state VI and the plutonium in oxidation state IV. Said process is characterised by the absence of any objective of homogeneity in the precipitate formed. The difference in U, Pu oxidation states results in a phenomenon of segregation, noted in the document, and which leads to a preferential precipitation of the plutonium, whereas the uranium remains to a non-negligible extent in solution.

The document of Atlas, "J. Nucl. Materials", 279(97), 46–51, concerns an oxalic coprecipitation process for U and Th. In this, it concerns an extremely specific case, because the existence of a single stable oxidation state (IV) of the thorium in solution leads to the absence of any possibility of redox reaction with U (IV), and thus the problem posed by the reaction (1) above, is not posed in the case of thorium. The process developed in said document is therefore useful for the manufacture of thorium cluster fuels (U, Th), but is absolutely not applicable, as such, for the production of other co-oxides, such as the co-oxides U, Pu, homogeneous for MOX fuel, since it does not guarantee that the oxidation state IV is maintained during the precipitation.

In other words, the sole aim of the process described in said document is the preparation by coprecipitation of co-oxides (U, Th). It cannot be applied to the preparation by coprecipitation of solid solutions (U, Pu) $O_2$ that are perfect for the manufacture of fuels, such as MOX fuel.

There is therefore a need, that has not yet been met, for a process that makes it possible to coprecipitate actinides in solution in oxidation state (IV), in particular in acid media.

In particular, there is a need for a process in which, in order to maintain the oxidation stage (IV) of the actinides in solution, and to obtain the coprecipitation of said elements effectively in oxidation state (IV), one destroys the mutual redox reaction of the actinides in solution.

In other words, there is a need for a process in which the actinides are maintained in solution in a same oxidation state IV, in such a way as to free them subsequently by coprecipitation into completely homologous compounds which will allow, after calcination, mixed homogeneous oxides coming close to a perfect solid solution, and not containing mineral impurities, to be obtained.

The aim of the present invention is to provide a process for coprecipitating (or simultaneous precipitating) actinides in oxidation state (IV) which meets, among other things, all of the requirements mentioned above and which satisfies the requirements, already cited above, for coprecipitation processes in general.

A further aim of the present invention is to provide a process for coprecipitating actinides in oxidation state (IV) which does not have the drawbacks, limitations, defects and disadvantages of the processes of the prior art and which resolve the problems of the prior art.

This aim, and others, are obtained, in accordance with the invention, by a process for coprecipitating (or simultaneous precipitating) actinides in oxidation state (IV) in which:

In a first embodiment of the process, which is the most general case, where the addition of the complexing agent does not ensure a thermodynamic stabilisation of the oxidation states (IV):

one adds an actinide (IV) selective organic complexing agent, and composed uniquely of oxygen, carbon, nitrogen and hydrogen atoms, to a first aqueous solution of an actinide $An^1$ in oxidation state IV in order to form a complex of the actinide $An^1$ in oxidation state IV;

one adds said complexing agent to at least one second aqueous solution of an actinide $An^2$ in oxidation state IV in order to form a complex of the actinide $An^2$ in oxidation state (IV);

one intimately mixes said at least first and second solutions of complexes;

one carries out the simultaneous precipitation of said at least two $An^1$ (IV) and $An^2$ (IV) actinide complexes from said mixture.

In a second embodiment of the process according to the invention, which is a specific case, where the addition of complexing agent ensures a thermodynamic stability in the mixture of actinides (IV)—and knowing that the redox reaction to consider corresponds to:

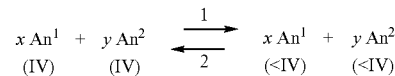

is spontaneous in direction 1, in the absence of the complexing agent and is observed in the direction 2 in the presence of the complexing agent—:

one intimately mixes a first aqueous solution of an actinide $An^1$ in an oxidation state less than IV and at least one second aqueous solution of an actinide $An^2$ in an oxidation state greater than IV;

one adds an actinide (IV) selective, organic complexing agent, and composed uniquely of oxygen, carbon, nitrogen and hydrogen atoms, to said mixture, in such a way as to spontaneously bring, by redox reaction, the at least two actinides $An^1$ and $An^2$ to the oxidation state IV and form complexes of actinides $An^1$ and $An^2$ in the oxidation state IV;

one carries out the simultaneous precipitation of said at least two actinide complexes $An^1$ (IV) and $An^2$ (IV).

The present invention is based on a new concept of kinetic stability of the oxidation states (IV), which does not necessarily require a thermodynamic stabilisation of the states (IV) of the actinides.

Therefore, this goes against the approach unanimously taken in the processes of the prior art.

Thanks to the complexing agents used according to the invention, without crossover of redox potentials, but by effect of "chemical gel", combined with the complexation of actinide IV cations, a sufficient stability is obtained, for a long time, which allows, among other things, for:

the intimate mixing of the solutions of $An^1$ (IV) and $An^2$ (IV) actinides;

the precipitation of the $An^1$ (IV) and $An^2$ (IV) complexes to subsequently take place in a perfectly simultaneous manner;

the spontaneous redox reaction does not take place during the two phases of mixing and precipitation.

Unlike the prior art, cited above, one produces, according to the invention, through a single homogeneous coprecipitation, perfectly homologous compounds, capable of then providing a mixed oxide, itself perfectly homogeneous.

The coprecipitation takes place from a mixture of at least two stable solutions, in which the actinides are constantly maintained in the state of $An^1$ (IV) and $An^2$ (IV), said at least two solutions being prepared in a complexing medium, either separately, or by spontaneous reaction, following the crossover of the normal apparent potentials of the redox pairs.

In other words, according to the invention, said actinide solutions (IV) may be prepared in homogeneous mixture by benefiting from:

either, in the general case, the kinetic stability obtained in the complexing medium, without crossover of redox potentials;

or thermodynamic stability, when the order of the normal potentials of the corresponding redox pairs is reversed.

In both cases, the stability obtained makes it possible to carry out the simultaneous precipitation of the actinides (IV).

It is obvious that, in addition to the advantages cited above, the process according to the invention also has all of the aforementioned advantages of precipitation processes.

The process of the invention fundamentally differs from the document "Atlas J. Nucl. Materials", cited above. In fact, the process of the invention is intended, in the first place, for the preparation of powders of oxides, such as (U, Pu), perfectly homogenous and suitable for the manufacture of fuels such as MOX. It can also be applied to the manufacture of other co-oxides of elements with oxidation states IV in solution, for example, ((Pu, Np), (Pu, Th), (U, Th), (U, Np), and their combinations (U, Pu, Np, Th).

Quite the reverse, the sole aim of the process of said document of the prior art, and the only thing it allows, is the production of co-oxides (U, Th). It is based on a fundamentally different concept to that of the process of the invention, and does not allow the production of a large variety of co-oxides covering virtually all of the actinides. The process of said document is extremely limited, it is based on a chemistry that is specific to the element thorium and which in no way can be transposed to the other actinides. In particular, said process cannot be applied to the preparation of perfectly homogeneous co-oxides, such as (U, Pu) for the production of fuels, such as MOX.

The process according to the invention applies, preferably, to the coprecipitation of two actinides, but it can also allow the coprecipitation of more than two actinides, for example, up to four actinides. In this case, one adds, in the case, for example, of the first embodiment of the invention, the complexing agent to each actinide solution, from the actinide solution $An^1$ up to the actinide solution $An^n$ in oxidation state (IV) in order to form each time an actinide complex, up to the $An^n$ actinide complex in oxidation state (IV), then one intimately mixes the n solutions and one carries out the simultaneous precipitation of said actinide complexes $An^1$ (IV), $An^2$ (IV), . . . $An^n$ (IV) from said mixture.

The second embodiment of the process of the invention applies in the same manner to n actinides. In the following description, the invention is generally described in the case of two actinides, but it will be understood that said description could apply to a number of actinides greater than 2.

In the first embodiment of the process of the invention, the complexing agent or organic ligand, used in the process, is an actinide (IV) selective, organic complexing agent, and composed uniquely of oxygen, carbon, nitrogen and hydrogen atoms.

As a result, unlike phosphotungstate type complexing agents, the complexing agents according to the invention meet the norm, called "CHON", in other words they only generate, when the precipitates are calcinated, gaseous decomposition products that can be rejected. The precipitates, according to the invention, may thus be used for producing mixed oxides constituting nuclear fuels, such as MOX.

Complexing agents, which meet these conditions and which thus allow the "kinetic gel" to be produced according to the invention, are known to those skilled in the art; they may be chosen from among polyamino carboxylic acids, carboxylic acids, the salts thereof, for example the ammonium or quaternary ammonium salts thereof, and the other complexing, chelating, organic agents that meet the "CHON" criteria.

Among the polyamino carboxylic acids, one may cite diethylene triamine pentacetic acid (DTPA), ethylene diamine tetraacetic acid (EDTA), cyclohexane diamine tetraacetic acid (CYDTA), hydroxyethyl ethylene diamine tetraacetic acid (EDTA-OH), triethylene tetramine hexaacetic acid (TTHA) and alkali metal salts thereof, for example lithium, sodium and potassium salts.

Among the carboxylic acids, the polycarboxylic acids, such as diacids and triacids and hydroxyacids are preferred.

One may cite, for example, oxalic acid, malonic acid, succinic acid, glutaric acid, tetrahydrofuran-2,3,4,5-tetra carboxylic acid (THFTCA), citric acid, lactic acid, glycolic acid, glyceric acid, tartric acid, malic acid, nitrilo acetic acid (NTA), hydroxyl ethylimino diacetic acid (HIDA) and ammonium or quaternary ammonium salts thereof.

Among the other complexing agents, organic chelating agents, one may cite hydroxamic acids, such as octane 1,8-dihydroxamic acid and cage molecules, such as 1,7-diaza-4, 10,13-trioxacyclopentadecane-N, N'-diacetic acid (K21DA), 1,4,7,10-tetraazacyclododecane-N, N', N'',N'''-tetraacetic acid (DOTA), the cryptands and other crown ethers.

The complexing agent most particularly preferred is oxalic acid and salts thereof, such as ammonium oxalate; in fact, its use brings about a series of specific additional advantages which will be explained below.

The first and second solutions of $An^1$ and $An^2$ actinides are generally acid aqueous solutions. Preferably, they are aqueous solutions of nitric acid.

The concentration of actinides $An^1$ and $An^2$, in each solution, can vary widely, but it is generally from 0.1 to 100 $g.l^{-1}$.

The ratio of the concentration in complexing agent to the concentration in each of the actinides $An^1$ and $An^2$ is generally from 1 to 60, and preferably from 1 to 20.

Said first and second solutions are generally mixed in a proportion that corresponds to the respective proportions of the two actinides $An^1$ and $An^2$ in a mixed oxide capable of being prepared by calcination, from the (co)precipitate obtained.

The process, in the mixing stage as much as in the simultaneous precipitation stage, is generally carried out between 0° C. and boiling, preferably at a temperature close to ambient, for example, from 20 to 60° C.

The simultaneous precipitation or coprecipitation of the actinides $An^1$ and $An^2$ is generally carried out through the addition to the mixture of an ammonium salt and/or a quaternary ammonium salt, of formula $NR_4^+$, where R is an alkyl group; said salt is, preferably, a nitrate that is generally in solution at ambient temperature, in a water/ethanol medium, in proportions generally of 30% water and 70% ethanol, by volume.

In one embodiment, the coprecipitation or simultaneous precipitation is carried out by acidification of the mixture.

Said acidification may be carried out, preferably, by addition of nitric acid to the medium.

The precipitation pH depends notably on the actinides and the complexing agents, but is generally from 0 to 1, and preferably the final acidity is close to 1 M.

In the second embodiment of the process of the invention, the first solution of an actinide $An^1$ in an oxidation state less than (IV) and the second solution of an actinide $An^2$ in an oxidation state higher than (IV) are generally acid aqueous solutions.

Preferably, they are aqueous solutions of nitric acid.

The concentration of actinides $An^1$ and $An^2$ in each of the solutions may vary widely, but is generally from $10^{-3}$ M to 1 M, and preferably from 0.1 to 0.2M.

Preferably, the actinide $An^1$ is in oxidation state (III) and the actinide $An^2$ is in oxidation state (VI).

Said first and second solutions are then intimately mixed in a proportion that corresponds to the respective proportions of the redox reaction that one wishes to obtain.

The molar ratio $An^1/An^2$ in the mixture will thus generally equal the ratio x/y, in accordance with the reaction:

$$xAn^1(<\text{IV})+y\,An^2(>\text{VI})\rightarrow xAn^1(\text{IV})+y\,An^2 \quad\quad (\text{IV})$$

This reaction is the inverse of the redox reaction, which is spontaneous in non-complexing media.

Moreover, it is necessary that the proportions of the mixture of the two solutions correspond to the proportions of the two actinides in a mixed oxide that could be prepared by calcination from the resulting coprecipitate.

The complexing agent or organic ligand, which is added to each of the at least two solutions, is an actinide (IV) selective, organic complexing agent, and composed uniquely of oxygen, carbon, nitrogen and hydrogen atoms.

The same complexing agents as those of the first embodiment may be used.

The ratio of the concentration in complexing agent to the total concentration of the at least two actinides in the mixture ($An^1+An^2$) is set in such a way as to conserve an excess of ligand.

The ratio of complexing agent/actinides ($An^1+An^2$) is generally from 1 to 40, and preferably from 1 to 5, and even more preferably, from 1 to 4.

Preferably, the pH of the mixture is adjusted in such a way as to favour the selective complexation of the oxidation states (IV).

One then carries out the coprecipitation or simultaneous precipitation under the same conditions as for the first (embodiment of the process.

The process, in said second embodiment, is generally carried out between 0° C. and boiling, and preferably from a temperature close to ambient, whether in the mixing stage, in the stage of adding the complexing agent or in the simultaneous precipitation stage.

The invention also concerns a process for preparing mixed oxides of $An^1$ and $An^2$ actinides, in which one coprecipitates said actinides by the process according to the invention, described above, whether in its first embodiment or in its second embodiment, and then one carries out the calcination of the (co)precipitate obtained thereof.

Because of the fact that, according to the process of the invention, the compounds obtained at the end of the coprecipitation are totally homologous compounds, the prepared mixed oxides, after calcination, are mixed oxides approaching a perfect solid solution.

The solid solutions of mixed oxide may, moreover, be obtained in any proportions.

The calcination is generally carried out under the following conditions: temperature equal to or greater than 650° C. under neutral or inert atmosphere (argon, etc.) and a time greater than or equal to 1 hour.

The $An^1$ and $An^2$ actinides are different and are each chosen from the group of actinides but, preferably, the $An^1$ and $An^2$ actinides are respectively uranium and plutonium.

As a result, the process according to the invention is, in the first instance, applicable to binary mixtures, but it can also be applied to multiple mixtures of more than two actinides.

The mixtures may be used, in particular, for the production of mixed uranium and plutonium type nuclear fuel, called MOX.

The oxide prepared, according to the invention, may be used either as a masterbatch of powders or as a mixture of powder at the final concentration. The continuation of the process for preparing MOX fuel pellets is known and traditionally comprises steps of pressing, fritting and precision grinding.

The process according to the invention may also advantageously be used for the production of transmutation targets (Np) or for the stable storage of materials (U, Pu, Np, Th) in the form of oxides. The oxides being prepared according to a similar procedure to those described below.

The process according to the invention is now going to be described in a detailed manner in the description that follows, given by way of illustration and in nowise limitative. The first embodiment of the process of the invention, which is the most general case, is described first.

One adds, in this case, first of all, a complexing ligand agent to a first aqueous solution of a first actinide $An^1$, which is in oxidation state (IV).

In general, the solution is an acid solution, preferably an aqueous solution of nitric acid.

The concentration in acid of the solution is generally from 1 M to 5 M, and preferably from 1 M to 3 M.

It should be noted that solutions likely to contain oxidising agents, such as nitric acid, nitrous acid, or likely to come in contact with them, such as the oxygen in the air, are generally stabilised by addition of one or several anti-nitrous compound(s), such as hydrazine, hydrazinium ions, or their derivatives.

The concentration in actinide $An^1$ in this solution is generally from $10^{-3}$ to 1 M, and preferably from 0.1 M to 0.2 M.

The ratio [ligand]/[$An^1$], for example [ligand]/[Pu], is determined by preliminary studies in solution. Said ratio is generally from 1 to 60; it is, for example, from 1 to 20 in the case of plutonium.

The complexing agent is chosen from among the compounds already cited above; it is chosen, preferably, from among oxalic acid and ammonium salts thereof.

In fact, when the effect of chemical gel is produced by the oxalic acid, the invention presents a series of additional specific advantages:

the reagent is already used in the "PUREX" process during the final conversion into oxide $PuO_2$ of the plutonium nitrate from purification cycles. Its use in a U, Pu coprecipitation process is, in principle, compatible with the existing apparatus in reprocessing plants. The decomposition of actinide oxalates is easy and generally leads to oxides having good sinterability;

the management of said reagent in the supernatants from these plants is today well controlled.

the same compound may ensure at the same time and successively the effect of chemical gel and the precipitation of actinides (IV), depending on the acidity of the medium;

a simple addition of nitric acid makes it possible to provoke the precipitation of the mixture of actinide (IV) complexes.

The pH range, in which is carried out the addition of the ligand, complexing agent, depends on the protonated forms of the ligand and is chosen in such a way as to form the higher ligand—$An^1$ (IV) complexes, for example ligand-Pu (IV). Generally, the pH range will be from 0 to 6 and, preferably, from 1 to 3.

In the same way that one has thus prepared a first solution of higher ligand—An (IV) complexes, one prepares, separately, preferably simultaneously, a second solution of higher ligand—$An^2$ (IV) complex, for example ligand—U (IV); said preparation is generally carried out under the same conditions as those described above for the first solution, by adapting, if necessary, the operating conditions, in order to form the higher ligand—$An^2$ (IV) complexes. It should be pointed out that generally the complexes of $An^1$ and $An^2$ formed have the same stoichiometry and that they therefore have the same behaviour in solution.

The concentration in actinides $An^2$, in the second solution, is generally from $10^{-3}$ to 1 M and, preferably, between 0.1 and 0.2 M.

Preferably, the two solutions are both aqueous solutions and preferably aqueous solutions of nitric acid. Their pH is normally adjusted between 1 and 3, in such a way as to come within the aforementioned range of formation of the desired complexes.

The two solutions of complexes thus obtained are intimately mixed, for example by means of an agitator.

By intimate mixing, it is understood that the medium is homogenous at the micro-mixing scale.

The time of this mixing stage is generally from 1 to 15 minutes, and said stage is carried out generally at the same temperature as the stage of preparing the solutions. The stability of the oxidation states IV in the previous complexes obtained in the first and second solutions, based according to the invention on a strong kinetic effect, is such that the mixture of the two solutions takes place, without being hindered by redox reactions, and without the oxidation state (IV) of the actinides $An^1$ and $An^2$ being affected.

In the mixture obtained, in the same way, the spontaneous reaction expected between $An^1$ (IV) and $An^2$ (IV) is completely inhibited and the solution forming the mixture is stable for a long time, which can be from 5 hours to 7 days. One therefore has a wide period for carrying out the final coprecipitation or simultaneous precipitation stage.

The mixing proportions of the two solutions are those that correspond to the ratios $An^1/An^2$ in the final mixed oxide.

The mixture may be carried out in any proportion (0<$An^1$/$An^2$<100%).

Thus, for example, in the case where one wishes, following the calcination, to obtain the mixed oxide of uranium and plutonium of formula $(U_{0.7}, PU_{0.3})O_2$, the proportion of the mixture of the two solutions of U (IV) and plutonium (IV) complex will be respectively 70% and 30%.

The following stage of the process according to the invention is the coprecipitation or simultaneous precipitation of the complexes of $An^1$ and $An^2$, for example U (IV) and Pu (IV). Said coprecipitation is carried out, according to the invention and due to the great stability of the complexes of $An^1$ and $An^2$, in a homogeneous manner and the calcination of the precipitate thus leads to a mixed oxide ($An^1$, $An^2$)$O_2$, for example (U, Pu)$O_2$ also perfectly homogeneous.

The simultaneous precipitation of $An^1$ (IV) and $An^2$ (IV), for which the choice depends, for example on the nature of the ligand, always maintained in a stable manner in oxidation state (IV), may be carried out by any known process, but preferably is carried out by addition to the mixture described above of an ammonium salt and/or quaternary ammonium salt $R_4N^+$; said salt may be chosen, for example, from halides, nitrates etc. The preferred salt is the nitrate, when the mixture comprises, for example, a nitric aqueous solution.

In the preceding formula, R generally represents a linear or branched alkyl group, generally from 1 to 12 atoms of carbon; examples of such groups are methyl, propyl, isopropyl, butyl, isobutyl, tertbutyl groups, etc.

Said precipitation is generally carried out in a water-ethanol medium in the proportions, by volume, of 30/70.

One uses, preferably, such a coprecipitation process when the ligand (L) is chosen among the polyamino carboxylic acids.

Another coprecipitation procedure consists in acidifying the mixture, for example by addition of nitric acid, in such a way as to attain the desired coprecipitation pH; said pH is thus generally from 0 to 1.

The process of coprecipitation by acidification of the mixture is used, preferably, when the ligand (L) is chosen from among the carboxylic acids.

The coprecipitation, generally carried out at the same temperature as the previous stages, in other words at a temperature from 0 to 60° C., gives a completely homogenous compound of formula (U, Pu)$L_x$,n$H_2O$, which is separated from the mixture by any appropriate means of liquid-solid separation, for example by filtration, centrifuging or other.

If one wishes to prepare a mixed oxide, the recovered coprecipitate is then calcinated to give the oxide ($An^1$, $An^2$)$O_2$, for example (U, Pu)$O_2$, and preferably under inert atmosphere, at a temperature of at least 650° C. (preferably, 950° C.) and for a minimum time of one hour (preferably, 2 hours or more).

Preferably, one reaches the final calcination temperature, for example, of 950° C., by carrying out temperature increases and by observing stages at fixed temperatures, for example, 150 and 600° C.

We will now describe the second embodiment of the process of the invention, which is a specific case, in which the complexing agent (meeting the CHON concept) used is sufficiently strong and selective for actinides in oxidation state IV, and where it is possible to operate as a variant of the general case according to the following specific description:

a first solution of actinide $An^1$ is in an oxidation state less than IV (it may be, for example, a nitric solution of plutonium III). The actinide concentration is generally from $10^{-3}$ to 1 M, and preferably between 0.1 and 0.2 M. The acidity is generally from 1 to 3 M;

a second solution of actinide $An^2$ is in an oxidation state greater than IV (it may be, for example, a solution of uranyl nitrate). The actinide concentration and the acidity are in the same range as previously;

the two solutions are intimately mixed in the proportions corresponding to those of the redox reaction that one wishes to obtain. For example, the ratio Pu III/U VI will be set at 2 in order to bring about the reaction U VI+2Pu III→U IV+2Pu IV, the inverse of the redox reaction which is spontaneous in non-complexing media;

the addition of the complexing agent to the previous mixture is carried out by setting the ratio ligand/ actinides ($An^1+An^2$), in such a manner as to maintain a slight excess of ligand.

Said excess is determined according to the composition of the limit complexes formed between the ligand L and the actinides $An^1$ and $An^2$ in oxidation state IV.

The pH of the solution is adjusted in such a way as to favour the selective complexation of the oxidation states IV; for example, for the actinide pair U VI, Pu III and if the choice of ligand L is DTPA, the pH can be set=1.45 and DTPA/$An^1+An^2$=1.25;

following the addition of the complexing agent, the redox reaction, making it is possible to obtain $An^1$ and $An^2$, in oxidation state IV, takes place spontaneously. In the case of U IV and Pu III, the reaction is total, in less than 24 hours.

The description of the following stages of the process, in said second embodiment, namely the precipitation, is then the same as in the first embodiment of the process, or general case, described above.

The invention will now be described in referring to the following examples, given by way of illustration and in nowise limitative.

EXAMPLE 1

In this example, one carries out the coprecipitation of U (IV) and Pu (IV), by means of DTPA (diethylene triamine pentacetic acid), as the complexing agent.

The operating conditions are as follows:
temperature: ambient temperature (20 to 26° C.);
[U (IV)]=[Pu (IV)]=0.008 M;
[DTPA]=0.01 M;
[$NO_3^-$]=1 M;
adjustment of the free acidity.

Under these conditions, one forms the limit complex 1/1 U (IV)-DTPA and Pu (IV)-DTPA.

The "chemical gel" effect obtained is such that when said two complexes are mixed in solution with all of the possible ratios U/U+Pu (U/U+Pu between 0 and 1), the solution remains stable over a period of at least 18 hours.

In the presence of hydrazinium ions [$N_2H_5$]=0.1 M, the stability of U IV and Pu IV in solution is more than 30 days. One thus has a long time available to carry out the precipitation operation after mixing the U and Pu.

In order to coprecipitate said two complexes in a homogeneous manner, a water-ethanol medium is used (30/70 by volume), while adjusting the pH to 7.5 by concentrated ammonia.

EXAMPLE 2

In this example, one carries out the coprecipitation of U (IV) and Pu (IV) by means of oxalic acid or ammonium oxalate, $H_2C_2O_4$ or $(NH_4)_2C_2O_4$.

The operating conditions are as follows:
temperature: ambient temperature (21 to 26° C.);
[U (IV)]=[Pu (IV)]=0.004 M;
[$C_2O_4^{2-}$]=0.08 M;
[$NO_3^-$]=1 M;
adjustment of the free acidity.

The stoichiometry of the limit complex is ¼, the complexes formed are the following: $U(C_2O_4)_4^{4-}$ and $Pu(C_2O_4)_4^{4-}$.

When said two complexes are mixed (with all U/U+Pu ratios between 0 and 1), their stability is ensured for at least 5 hours. After this time, one sees, by UV—visible spectrophotometry, the complex $U(C_2O_4)_4^{4-}$ disappear. The disappearance of said complex is complete within 5 days without however the characteristic spectrum of the complex $Pu(C_2O_4)_4^{4-}$ being heavily modified.

When conserved under an oxygen free atmosphere, the stability of the previous mixture exceeds 5 days.

In order to coprecipitate said two complexes in a homogeneous manner, one can employ two methods:
either a water-ethanol medium is used (30/70 by volume),
or one adds nitric acid to the mixture.

In the second case, the precipitation conditions are as follows:
$HNO_3$ 1 M medium, i.e. pH=0
simultaneous precipitation of uranium (IV) and plutonium (IV) in oxalate medium.

It is not necessary to increase the concentration of nitric acid, which would induce the uranium (IV) and the plutonium (IV) being put into solution and thus the formation of uranium (VI) and plutonium (III) (species observed by spectrophotometry).

The precipitation yield for each actinide (IV) is greater than 95%.

EXAMPLE 3

In this example, one carries out the coprecipitation of U (IV) and Pu (IV) by means of NTA (nitrilo acetic acid)

The operating conditions are as follows:
temperature: ambient temperature (21<T° C.<26° C.);
[U (IV)]=[Pu (IV)]=0.001 M;
[NTA]=0.006 M;
[$NO_3^-$]=1 M;
adjustment of the free acidity.

The stoichiometry of the limit complex is 1/1, and the following complexes are formed: U (NTA) and Pu (NTA) Said complexes are formed in the pH range 5 to 7, whereas around pH=1.1 other species appear: notably An $(HNTA)^{2+}$. When the two limit complexes are mixed with all U/U+Pu ratios between 0 and 1, around pH=6, their stability is ensured for at least one hour.

In order to coprecipitate said two complexes in a homogeneous manner, an efficient method is provided in water-ethanol medium (30/70 by volume), while adjusting the pH to a value above 7 by adding a concentrated base.

Table I shows the data relative to the stages of formation in solution of the higher complexes of uranium (IV) and plutonium (IV):

TABLE I

Operating conditions for forming higher complexes of uranium (IV) and plutonium (IV) with oxalic acid, DTPA and NTA.

| Ligand | $H_2C_2O_4$ | DTPA | NTA |
|---|---|---|---|
| [Ligand]/[An (IV)] minimum | 4 | 1 | 1 |
| pH range | 1.5 < pH < 3 | 2 < pH < 4 | 5 < pH < 7 |

In the three examples cited above, it has been shown that thanks to the process of the invention one has been able to inhibit the spontaneous reaction between U (IV) and Pu (IV).

EXAMPLE 4

This example illustrates the specific case of the second embodiment of the invention, where the thermodynamic stability of the oxidation states IV within the mixture may be obtained.

The operating conditions are as follows:
temperature: ambient temperature (21 to 26° C.);
[U (VI)]=0.0022 M.
[Pu (III)]=0.0044 M;
[DTPA]=0.008 M;
[$NO_3^-$]=1 M;
[$N_2H_5^+$]=0.1 M;
pH=1.45.

At said pH, U (VI) is partially complexed and Pu nearly completely complexed by the DTPA in the form of 1-1 complexes. The DTPA is slightly in excess and the ratio Pu/U is selected to equal 2.

Under these conditions, one observes the progressive oxidation of the Pu III-DTPA into Pu IV-DTPA, whereas simultaneously there is the reduction of U VI-DTPA into U IV-DTPA.

The reaction U (VI)-DTPA+Pu (III)-DTPA→U (IV)-DTPA+Pu (IV)-DTPA is complete after 10.5 hours. After this time period, only the 1-1 non-protonated complexes of Pu IV-DTPA and U IV-DTPA are observable by UV-visible spectrophotometry. The ratio Pu/U in said mixture of two complexes is maintained equal to 2.

The coprecipitation of the mixture thus obtained is then similar to that described in example 1.

EXAMPLE 5

In this example, one carries out the calcination of the precipitates obtained in examples 1 to 4 under the following calcination conditions:

raising the temperature from ambient temperature in order to reach, at a rate of 10° C. per minute, the temperature of 150° C., namely after a heating time of around 15 minutes;
maintaining the temperature at 150° C. for 20 minutes;
raising the temperature from the stage at 150° C., at a rate of 10° C. per minute, for 45 minutes;
maintaining the temperature at 600° C. for 40 minutes;
raising the temperature from the stage at 600° C., at a rate of 15° C. per minute, for 23 minutes;
finally maintaining the temperature at 950° C. for 2 hours.

After the final 2 hour calcination operation at 950° C., the oxide resulting from the decomposition of the precipitate may be characterised by X-ray diffraction.

It has thus been proven that, in all of the cases (examples 1 to 4), whatever the initial U, Pu mixture in solution, the mixed oxide formed is homogeneous and in the same U/Pu proportions as the initial mixture in solution.

The invention claimed is:

1. A process for coprecipitating actinides in oxidation state (IV) in which:
    adding an actinide (IV) selective organic complexing agent and composed uniquely of atoms selected from the group consisting of oxygen, carbon, nitrogen and hydrogen, to a first aqueous solution of an actinide $An^1$ in oxidation state (IV) in order to form a complex of the actinide $An^1$ in oxidation state (IV);
    adding said complexing agent to at least one second aqueous solution of an actinide $An^2$ in oxidation state (IV) in order to form a complex of the actinide $An^2$ in oxidation state (IV);
    intimately mixing said at least first and second solutions of complexes;
    simultaneously precipitating said at least two $An^1$ (IV) and $An^2$ (IV) actinide complexes from said mixture.

2. Process according to claim 1, in which said complexing agent is at least one member selected from the group consisting of polyamino carboxylic acids, carboxylic acids, salts of polyamino carboxylic acids, salts of carboxylic acids and other complexing, chelating, and organic agents.

3. The process according to claim 2, in which said complexing agent is a polycarboxylic acid.

4. The process according to claim 3, in which said polycarboxylic acid is at least one selected from the group consisting of oxalic acid, malonic acid, succinic acid, glutaric acid, citric acid, lactic acid, glycolic acid, glyceric acid, tartric acid, malic acid, ammonium salts thereof, and quaternary ammonium salts thereof.

5. The process according to claim 3, wherein the polycarboxylic acid is a diacid, triacid, or hydroxyacid.

6. The process according to claim 2, in which said complexing agent is at least one member selected from the group consisting of tetrahydrofuran-2,3,4,5-tetracarboxylic acid (THFTCA), nitrilo acetic acid (NTA), hydroxy ethylimino acetic acid (HIDA), ammonium salts thereof, and quaternary ammonium salts thereof.

7. The process according to claim 2, in which said complexing agent is at least one member selected from the group consisting of hydroxamic acids, cage molecules, cryptands and crown ethers.

8. The process according to claim 7, wherein the complexing agent is a hydroxamic acid and is octane 1,8-dihydroxamic acid.

9. The process according to claim 7, wherein the complexing agent is a cage molecules and is 1,7-diaza-4,10,13-trioxacyclopentadecane-N, N'-diacetic acid (K21DA), or 1,4,7,10-tetraazacyclodecane-N, N', N'', N'''-tetraacetic acid (DOTA).

10. The process according to claim 1, in which said complexing agent is at least one member selected from the group consisting of diethylene triamine pentacetic acid (DTPA), ethylene diamine tetraacetic acid (EDTA), cyclohexane diamine tetraacetic acid ( CYDTA), hydroxyethyl ethylene diamine tetraacetic acid (EDTA-OH), triethylene tetramine hexaacetic acid (TTHA) and alkali metal salts thereof.

11. The process according to claim 10, wherein the complexing agent is a salt and is at least one salt selected from the group consisting of lithium, sodium and potassium salts.

12. The process according to claim 1, in which said at least first and second solutions are acid solutions.

13. The process according to claim 12, in which said at least first and second solutions are aqueous solutions of nitric acid.

14. The process according to claim 1, in which the concentration of actinides $An^1$ and $An^2$ in each of the first and second solutions is from 0.1 to 100 g.l$^{-1}$.

15. The process according to claim 1, in which the ratio of the concentration of complexing agent to the concentration of each of the actinides $An^1$ and $An^2$ is from 1 to 60.

16. The process according to claim 15, wherein the ratio is from 1 to 20.

17. The process according to claim 1, in which said at least first and second solutions are mixed in a proportion that corresponds to the respective proportions of the two actinides $An^1$ / $An^2$ in a mixed oxide capable of being prepared by calcination from a coprecipitate.

18. The process according to claim 1, in which the process is carried out at a temperature between 0° C. and boiling.

19. The process according to claim 1, in which the simultaneous precipitation is carried out by adding to the mixture an ammonium salt and/or a quaternary ammonium salt $NR_4^+$, where R is an alkyl group.

20. The process according to claim 19, in which said ammonium salt and/or quaternary ammonium salt is in solution of a water/ethanol medium.

21. The process according to claim 20, wherein the ammonium salt and/or quaternary ammonium salt is a nitrate.

22. The process according to claim 1, in which the simultaneous precipitation is carried out by acidification of the mixture.

23. The process according to claim 1, in which $An^1$ is Pu and $An^2$ is U.

24. The process according to claim 1, in which said complexing agent is at least one member selected from the group consisting of diethylene triamine pentacetic acid (DTPA), ethylene diamine tetraacetic acid (EDTA), cyclohexane diamine tetraacetic acid (CYDTA), hydroxyethyl ethylene diamine tetraacetic acid (EDTA-OH), triethylene tetramine hexaacetic acid (TTHA) and alkali metal salts thereof.

25. The process according to claim 24, wherein the complexing agent is a salt and is at least one salt selected from the group consisting of lithium, sodium and potassium salts.

26. A process for coprecipitating actinides in oxidation state (IV) in which:
intimately mixing a first aqueous solution of an actinide $An^1$ an oxidation state less than IV and at least one second aqueous solution of an actinide $An^2$ in an oxidation state greater than IV;
adding an actinide (IV) selective, organic complexing agent, and composed uniquely of atoms selected from the group consisting of oxygen, carbon, nitrogen and hydrogen, to said mixture, in such a way as to spontaneously bring, by redox reaction, the at least two actinides $An^1$ and $An^2$ to the oxidation state IV and form complexes of actinides $An^1$ and $An^2$ in oxidation state IV; simultaneously precipitating said at least two actinide complexes $An^1$ (IV) and $An^2$ (IV).

27. The process according to claim 26, in which the concentration of actinides in the at least first solution and second solution is from 10$^{-3}$ M to 1 M.

28. The process according to claim 27, wherein the concentration is from 0.1 to 0.2 M.

29. The process according to claim 26, in which the ratio of the concentration of complexing agent to the total concentration of at least two actinides in the mixture is from 1 to 40.

30. The process according to claim 29, wherein the ratio is from 1 to 20.

31. The process according to claim 29, wherein the ratio is from 1 to 5.

32. The process according to claim 29, wherein the ratio is from 1 to 4.

33. The process according to claim 26, in which the actinide $An^1$ has an oxidation state (III) and the actinide $An^2$ has an oxidation state (VI).

34. The process according to claim 26, in which said complexing agent is at least one member selected from the group consisting of polyamino carboxylic acids, carboxylic acids, salts of polyamino carboxylic acids, salts of carboxylic acids, and other complexing, chelating, and organic agents.

35. The process according to claim 34, in which said complexing agent is a polycarboxylic acid.

36. The process according to claim 35, in which said complexing agent is at least one selected from the group consisting of oxalic acid, malonic acid, succinic acid, glutaric acid, citric acid, lactic acid, glycolic acid, glyceric acid, tartric acid, malic acid, ammonium salts thereof, and quaternary ammonium salts thereof.

37. The process according to claim 35, wherein the polycarboxylic acid is a diacid, triacid, or hydroxyacid.

38. The process according to claim 34, in which said complexing agent is at least one member selected from the group consisting of tetrahydrofuran-2,3,4,5-tetracarboxylic acid (THFTCA), nitrilo acetic acid (NTA), hydroxy ethylimino acetic acid (HIDA), and ammonium salts thereof, and quaternary ammonium salts thereof.

39. The process according to claim 34, in which said complexing agent is at least one member selected from the group consisting of hydroxamic acids, cage molecules, cryptands and crown ethers.

40. The process according to claim 39, wherein the complexing agent is a hydroxamic acid and is octane 1,8-dihydroxamic acid.

41. The process according to claim 39, wherein the complexing agent is a cage molecules and is 1,7-diaza-4,10,13-trioxacyclopentadecane-N, N'-diacetic acid (K21DA), or 1,4,7,10-tetraazacyclodecane N, N', N", N"'-tetraacetic acid (DOTA).

42. The process according to claim 26, in which said first and second aqueous solutions are acid solutions.

43. The process according to claim 42, in which said first and second aqueous solutions are aqueous solutions of nitric acid.

44. The process according to claim 26, in which said first and second aqueous solutions are mixed in a proportion that corresponds to the respective proportions of the two actinides $An^1$ / $An^2$ in a mixed oxide capable of being prepared by calcination from the coprecipitate.

45. The process according to claim 26, in which the process is carried out at a temperature between 0° C. and boiling.

46. The process according to claim 26, in which the simultaneous precipitation is carried out by addition to the mixture of an ammonium salt and / or a quaternary ammonium salt $NR_4^+$, where R is an alkyl group.

47. The process according to claim 46, in which said ammonium salt and/or quaternary ammonium salt is in solution of a water / ethanol medium.

48. The process according to claim 47, wherein the ammonium salt and/or quaternary ammonium salt is a nitrate.

49. The process according to claim 26, in which the simultaneous precipitation is carried out by acidification of the mixture.

50. The process according to claim 26, in which $An^1$ is Pu and $An^2$ is U.

51. A process for preparing mixed oxides of actinides $An^1$ and $An^2$, comprising coprecipitating said actinides in oxidation state (IV) by the process according to claim 1, then calcinating the resulting precipitate.

52. The process according to claim 51, in which the calcinating is carried out under an inert or neutral atmosphere, at a temperature equal to or greater than 650° C. and for a time greater than or equal to 1 hour.

53. A process for preparing mixed oxides of actinides $An^1$ and $An^2$, comprising coprecipitating said actinides in oxidation state (IV) by the process according to claim 26, then calcinating the resulting precipitate.

54. The process according to claim 53, in which the calcinating is carried out under an inert or neutral atmosphere, at a temperature equal to or greater than 650° C. and for a time greater than or equal to 1 hour.

\* \* \* \* \*

UNITED STATES PATENT AND TRADEMARK OFFICE
CERTIFICATE OF CORRECTION

PATENT NO. : 7,169,370 B2 Page 1 of 1
APPLICATION NO. : 10/381592
DATED : January 30, 2007
INVENTOR(S) : Mesmin et al.

It is certified that error appears in the above-identified patent and that said Letters Patent is hereby corrected as shown below:

On the title page, Item (75), the Inventors information is incorrect. Item (75) should read:

-- (75) Inventors: Claire Mesmin, Le Garric (FR); Alain Hanssens, Tresques (FR); Charles Madic, Thiais (FR); Pierre Blanc, Les Angles (FR); Marie-Francoise Debreuille, Marcoussis (FR) --

Signed and Sealed this

Tenth Day of April, 2007

JON W. DUDAS
*Director of the United States Patent and Trademark Office*